(12) United States Patent
Niethammer

(10) Patent No.: US 8,208,994 B2
(45) Date of Patent: Jun. 26, 2012

(54) COMPUTER TOMOGRAPH AND INJECTOR HAVING A DATA INTERFACE

(75) Inventor: Matthias Niethammer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1806 days.

(21) Appl. No.: 10/553,627

(22) PCT Filed: Jan. 17, 2005

(86) PCT No.: PCT/EP2005/050171
§ 371 (c)(1),
(2), (4) Date: Oct. 19, 2005

(87) PCT Pub. No.: WO2005/070294
PCT Pub. Date: Aug. 4, 2005

(65) Prior Publication Data
US 2006/0224066 A1    Oct. 5, 2006

(30) Foreign Application Priority Data
Jan. 22, 2004    (DE) .......................... 10 2004 003 371

(51) Int. Cl.
*A61B 6/00* (2006.01)
*A61B 5/055* (2006.01)

(52) U.S. Cl. ....................................... 600/431; 600/425

(58) Field of Classification Search .................. 600/407, 600/420, 425, 431; 700/275
See application file for complete search history.

(56) References Cited

U.S. PATENT DOCUMENTS
2001/0009994 A1    7/2001    Small et al.
2002/0071521 A1    6/2002    Ohishi
2002/0165445 A1   11/2002    Uber, III et al.

FOREIGN PATENT DOCUMENTS
DE    195 33 557 C1    11/1996
JP    01 207 038 A     8/1989
JP    2004-298610      10/2004

OTHER PUBLICATIONS
Int'l Search Report.

*Primary Examiner* — Michael Rozanski
(74) *Attorney, Agent, or Firm* — Harness, Dickey & Pierce, P.L.C.

(57) ABSTRACT

A device and a method are for operating a computer tomograph and an injector, wherein an injector is used to control injection of a contrast medium and a computer tomograph to control a scanning process. Data regarding operation are transmitted between the computer tomograph and the injector via a data interface, especially in a reciprocal manner. The two devices reciprocally influence their operation, thereby reducing the strain imposed on a patient to be examined, increasing operational reliability and simplifying handling.

21 Claims, 1 Drawing Sheet

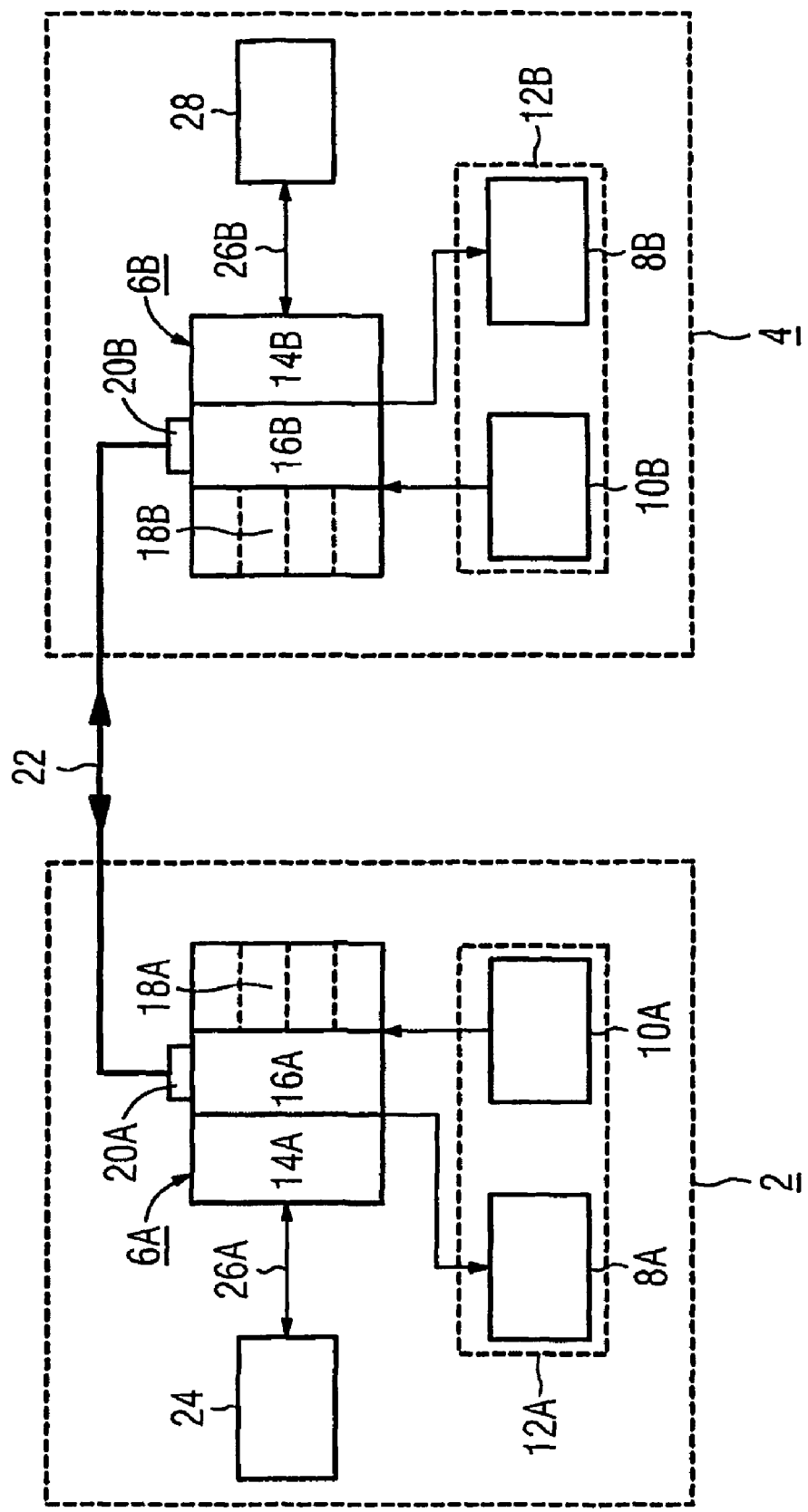

COMPUTER TOMOGRAPH AND INJECTOR HAVING A DATA INTERFACE

This application is the national phase under 35 U.S.C. §371 of PCT International Application No. PCT/EP2005/050171 which has an International filing date of Jan. 17, 2005, which designated the United States of America and which claims priority on German Patent Application number DE 10 2004 003 371.4 filed Jan. 22, 2004, the entire contents of which are hereby incorporated herein by reference.

FIELD

The invention generally relates to a method for data exchange between a computed tomograph and an injector, and/or to an apparatus including at least two devices.

BACKGROUND

When a patient is being examined via computed tomography, he/she is injected with a contrast agent via an injection system, denoted as injector below for short. The contrast agent serves the purpose of more effective visualization of the organ to be examined, which is transilluminated by X-rays in the computed tomograph. Images with the aid of which a doctor can undertake a diagnosis are generated via an imaging system from the X-ray signals acquired by a detector.

Both the X-radiation of the computed tomograph and the contrast agent injected via the injector impose a burden on the patient to be examined. Both the burden owing to X-radiation and the burden owing to the contrast agent must therefore be kept as light as possible. Consequently, it is normally only the mandatory quantity of contrast agent that is injected.

It is decisive here for the quality of imaging via the computed tomograph that the scanning operation of the computed tomograph be carried out at the correct instant. The correct instant is reached as a rule when the organ to be examined has been reached as desired by the injected contrast agent. In order to impose as little burden as possible on the patient, the radiation dose should be as light as possible, in addition.

DE 195 33 557 C1 discloses a method in which a suitable instant for the start of the scanning operation can be determined in a comparatively gentle way.

The level of the burden on the patient, and the quality of the images obtained are decisively codetermined also by the operating staff, who must operate the two devices, the computed tomograph, on the one hand and the injector, on the other hand, in a suitable way. Particularly in the case of the occurrence of malfunctions at one of the two devices, the experience and the reaction of the operating staff sometimes exerts considerable influence on the burden on the patient owing to the radiation or the contrast agent.

US 2001/0009994 A1 discloses an injector provided in particular for the application of a contrast agent. The injector can be connected via a data interface to an imaging system, in particular a computed tomograph, in order to enable data exchange between two devices or automated driving of the injector and/or the imaging system.

Likewise disclosed in the English language patent abstract JP 01207038 A is a computed tomograph that is connected via a data interface to an injector provided for the application of a contrast agent. Here, the injector is driven automatically by a control device of the computed tomograph. Further arrangements in the case of which a data exchange is performed between a computed tomograph and an injector are disclosed, for example, in US 2002/0165445 A1 or US 2002/0071521 A1.

SUMMARY

At least one embodiment of the invention includes an object of enabling improved operation of a computed tomograph and an injector.

Consequently, the two devices communicate with one another via the data interface such that their respective operation, that is to say the carrying out of the scanning operation, on the one hand, and the injection of the contrast agent, on the other hand, can be suitably coordinated overall with one another. The two devices can be coordinated with one another, particularly with regard to the starting operation of the examination and given the occurrence of a malfunction, by the exchange of current operationally relevant data. Furthermore, the linking of the two devices via the data interface offers the possibility to coordinate the two devices more effectively with one another even during the investigation, and to transmit the data obtained during the investigation from one device to the other device in an automatic fashion, for example for a patient-specific evaluation.

By coordinating the devices, it is possible, in particular, to reduce maloperations and to achieve an improved use of the devices with regard to the lightest possible burden on the patient.

A mutual control of the devices on the occurrence of a malfunction of one of the devices is performed in the course of the examination, that is to say of the scanning operation by the computed tomograph, on the one hand, and the injection by the injector, on the other hand. This malfunction is transmitted to the other device and displayed there, for example, such that, in particular, manual intervention by the operating staff is also enabled.

Consequently, by transmitting and displaying the malfunction of the injector, for example, through a display element of the computed tomograph the operating staff need only keep an eye on the display element of the computed tomograph in order to be able to detect a malfunction at an early stage and to react suitably.

Conversely, the operating state of the computed tomograph can also be displayed on a display element of the injector. Particularly in the case of failure or termination of the scanning operation and/or of the injection, it is possible thereby for the entire examination to be terminated manually at an early stage in order to keep the burden on the patient light.

In the presence of the malfunction a decision is made preferably automatically with the aid of a termination rule as to whether the operation of the other device is terminated or continued. It can be provided thereby, on the one hand, that a termination signal that prompts the operating staff to terminate manually is output acoustically, for example. With this variant, the final decision on the termination of the examination remains with the doctor or operating staff. That is to say, merely automatically in order to support the operating staff it is therefore merely automatically determined whether the termination would be expedient in accordance with the termination rules. As an alternative to this, the examination is, moreover, expediently terminated automatically and independently without the possibility of exerting influence.

Furthermore, the two devices mutually exchange data relating to their respective operating state. The data connection between the two devices is therefore bidirectional such that mutual monitoring is also possible, in particular.

In accordance with an example development, the data transmitted by one device may be used as a basis to control the operation of the other device. One device therefore directly influences the other device. Necessary control measures at one device, caused by a specific operating state of the other device, are therefore undertaken automatically without need for manual intervention by the operating staff.

It is expedient here to provide at the beginning of the examination that before starting to operate one device the operational readiness of the other device is checked.

If one of the devices is not operationally ready, the start of the operation of the other device may be, for example, automatically suppressed. The automatic suppression can include a delay until the other device is operationally ready, or in a complete termination such that both devices have to be restarted once more. Thus, for example, it is automatically investigated upon starting the computed tomograph whether the injector is operationally ready. Conversely, it is checked upon starting the injector as to whether the computed tomograph is operationally ready for carrying out the scanning operation. Unnecessary burdens on the patient owing to contrast agent and/or to X-radiation are avoided by these starting operations that are coordinated with one another.

Given the presence of a malfunction, decision parameters may be provided for taking a decision as to whether termination should be performed. The values for these decision parameters are determined here, in particular, from one or more of the following criteria, and used for the termination rule:

Values are automatically adopted from the operating data of at least one of the devices. Thus, for example, the quantity of the contrast agent already injected is an important criterion.

It is expedient also to take account of manually input values for the termination rule. Thus, it can be expedient for the doctor to specify up to which quantity of contrast agent, referred to the total quantity to be prescribed, a termination is to be performed. This manually prescribed value is then used to terminate the examination automatically upon undershooting of the value.

Organ-specific termination criteria are preferably also taken into account, that is to say different termination responses are advantageous for different organs.

A substantial influence on the need for a termination can also be exerted by patient-specific data such as, for example, weight, size, circulation etc. which are likewise taken into account for reaching a decision.

A further criterion are expediently the checking of characterizing protocols, that is to say the method cycles, such as injection rate, scanning rate, intensity of the X-radiation, for example, that characterize the scanning operation or the injection.

In order to facilitate the operation and monitoring, it is provided in accordance with an advantageous development that at least some essential operating data of one device are displayed on a display element at the other device. Moreover, it is advantageous when a common operating console that can also be used to drive the injector is provided at one of the devices, for example at the computed tomograph. In particular, this provides the possibility to also start or manually terminate the injector from the operating console of the computed tomograph.

In order to enable the mutual coordination of computed tomographs and injectors even of different types with one another, in an advantageous refinement the data interface is designed as a standardized interface. It is therefore possible even for different types of device to be connected to one another without any problem. The standardized and normalized data exchange here preferably provides a basis for a uniform operation and a uniform operator interface for different types of devices, as well. This simplifies the operation even of different types of device. A further advantage of the normalized and standardized communication between two devices resides in the possibility of coordinating the device parameters with one another between the computed tomograph and the injector for example when exchanging an injector. The device parameters of one device are respectively read out by the other device and evaluated.

For the purpose of a simplified evaluation of the examination results, an expedient development provides that a scanning-specific or injection-specific data protocol is transmitted from one device to the other device after the scanning operation or the injection has been carried out. Thus, for example, the computed tomograph inputs into its memory the data protocolled or stored during the injection by the injector, and there is advantageously set up a common data protocol that combines with one another the values of the computed tomograph and those of the injector, in particular via a common time axis.

BRIEF DESCRIPTION OF THE DRAWINGS

An example embodiment of the invention is explained in more detail with the aid of the figure.

The sole FIGURE shows a computed tomograph and an injector in a schematic, greatly simplified block diagram illustration.

DETAILED DESCRIPTION OF THE EXAMPLE EMBODIMENTS

A computed tomograph 2 and an injector 4 have comparable functional components in the example embodiment. The comparable functional components of the computed tomograph 2 are marked in the figure with the letter A, and those of the injector 4 are marked with the letter B.

The two devices respectively have a computed device 6A, B to which a display element 8A, B and an input element 10A, B are connected. Control signals are transmitted to the computed device 6A, B via the input element 10A, B, for example a keyboard, switch or the like. The display element 8A, B and the input element 10A, B may be combined in a uniform operating console 12A, B.

A number of functions are combined, in turn, in the computed device 6A, B. Thus, said device has a control device 14A, B, an evaluation device 16A, B, and a memory 18A, B that is, in turn, subdivided into a number of partial memories. Furthermore, the computed device 6A, B is allocated a standardized data interface 20A, B represented in the figure as a blackbox. Two computed devices 6A, B, and two devices 2, 4 are interconnected for data exchange via a common data line 22 and via the data interfaces 20A, B, and can exchange data with one another alternatively, that is to say bidirectionally, as illustrated by the arrows of the data line 22.

The computed device 6A of the computed tomograph 2 is further connected to a measuring system 24 via which the actual X-ray examination is undertaken with the aid of the computed tomograph 2. The measuring system 24 here includes, in particular, an X-radiation source and a detector arrangement for detecting the X-rays passing through an irradiated organ of a patient.

The values measured by the measuring system 24 are transmitted via a line 26A to the computed device 6A and evaluated there in the evaluation device 16A. The measuring system 24 is driven, for example, after being triggered via the input element 10A via the control device 14A.

In a way comparable to the measuring system 24 of the computed tomograph 2, the injector 4 has an injection system 28 that is connected to the computed device 6B via a line 26B.

Here, as well, the computed device 6B drives the injection system 28 and, if appropriate, evaluates the values obtained from the injection system 28. A contrast agent is injected via the injection system 28 in a way controlled in terms of time and quantity.

The interaction of the two devices 2, 4 is crucial when examining a patient, in order in particular to keep light the burden placed on the patient by the contrast agent, on the one hand, and/or by the X-radiation, on the other hand, and to avoid unnecessary burdens. The common data line 22 via the data interfaces 20A, B is of particular significance for the mutual coordination of the two devices 2, 4 with one another.

A bidirectional data exchange between the two devices 2, 4 is performed via the data line 22, which need not necessarily be cable-based. The devices therefore communicate with one another via the data line 22. In particular, the data transmitted, for example, by the injector 4 to the computed tomograph 2 influence the operation of the latter. That is to say, the driving of the measuring system 24 is also influenced by the data transmitted by the injector 4. This holds equally in the reverse direction for the injector 4, that is to say the driving of the injection system 28 is also influenced via the data transmitted by the computed tomograph 2 to the injector 4.

The mutual data exchange takes place, in particular, during the overall time duration of an examination. Here, examination is understood as the beginning, the carrying out and the ending as well as the evaluation of a scanning operation of the computed tomograph 2 and of the injection of the contrast agent by the injector 4. The mutual data exchange can be subdivided into the following four substages:
 a) starting phase;
 b) running examination, that is to say carrying out the scanning operation, on the one hand, and the injection, on the other hand;
 c) termination in the event of a malfunction of one of the two devices 2, 4;
 d) evaluation of the data obtained in the examination.

It is crucial in the starting phase that both devices 2, 4 be operationally ready to take up the actual operation, that is to say for the start of the scanning operation, on the one hand, or the injection, on the other hand. Until operational readiness is reached, the devices 2, 4 usually require a certain set-up time, or it is necessary to perform a few preparatory tasks such as, for example, providing the contrast agent etc.

As soon as a device is operationally ready, something which is indicated by an appropriate pilot lamp, for example, this device can be started in principle by a starting function, that is to say the scanning operation or the injection is executed. If the start is now triggered via the input elements 10A, B at one of the devices 2, 4, this device 2, 4 firstly enquires, via the data line 22, at the other device 2, 4 as to whether the latter is likewise operationally ready. If not, the operation is terminated and the start of the scanning operation or the injection is suppressed. After termination of the starting operation, the two devices 2, 4 must, in particular, be rendered operationally ready again. Only then is the new start of the scanning operation or of the injection possible.

In order to facilitate the operation and the monitoring of the examination, some relevant operating states of the injector 4 are displayed, in particular, at the display element 8A of the computed tomograph 2. These are, for example, the operational readiness important for the starting phase, the quantity of contrast agent already injected, the display of the quantity of contrast agent to be dosed per time device (contrast agent rate) as well as information relating to the current contrast agent delivery. Moreover, it is expediently provided for a simplified operation that also at least some basic functions of the injector 4 can be triggered via the input element 10A at the computed tomograph 2. Thus, for example, it is possible to start or to terminate the injector 4 via the input element 10A of the computed tomograph 2. Moreover, further functionalities of the injector 4 can also be driven from the computed tomograph 2, such as the setting of the contrast agent rate.

In addition to the starting phase, a further particularly critical phase with regard to the lightest burden possible on the patient is the termination phase when a malfunction occurs at one of the devices 2, 4 during the scanning operation or the injection. In particular, given the occurrence of a malfunction the question arises as to whether the entire examination must be terminated, or whether results that can still be used are to be expected despite the malfunction. The termination of the scanning operation at the computed tomograph or of the injection at the injector 4 is considered below as malfunction.

In the case of a termination of the scanning operation, it is senseless to carry on the injection, and the injection is switched automatically as a result. This is performed, for example, by communicating via the data line 22 to the injector 4 that the computed tomograph 2 has failed. This information is then evaluated in the computed device 6B, and the injection is automatically switched off. As an alternative thereto, the evaluation can already be performed in the computed device 6A, and the injector is then necessarily switched off from the computed tomograph 2.

Given failure of the injector 4, it is more difficult to reach a decision as to whether the entire examination is to be terminated. The decision as to whether termination is necessary depends here on a number of factors that influence one another mutually such that the decision cannot be taken straight away. In particular, because of the various parameters that interact with one another it is only possible with difficulty for the operating staff to arrive at a decision manually. A significant decision parameter here is, in particular, the quantity of the contrast agent already injected.

Also decisive in addition is which organ is being examined, or the examination protocol in accordance with which the examination is being executed, that is to say which method parameters are set for the scanning operation, on the other hand, and for the injection operation, on the other hand. Patient-specific data also exert an influence, of course.

Stored in at least one of the computed devices 6A, B is a termination rule or a termination program that automatically takes a decision in the light of the decision parameters as to whether or not a termination is expedient. If the system automatically detects that a termination of the entire investigation is expedient, this is indicated acoustically. The operating staff are thereby called upon, as it were, to terminate. In this variant, the decision on the termination finally remains with the operating staff. As an alternative to this, the termination is performed automatically and cannot be influenced by the operating staff.

At least some of the values for the decision parameter are automatically adopted thereby from the current operating data, particularly with reference to the quantity of contrast agent injected. Further values are adopted from organ-specific items of information stored in the memory 18A, B. Moreover, further values such as, for example, patient-specific data or the input up to which quantity of contrast agent a termination is to be performed are acquired manually.

The result of the automatically generated decision as to whether a termination is to be performed is that the operational validity is increased, operation is simplified, the operating staff are relieved and, in particular, an unnecessary burden on the patient from contrast agent is effectively prevented.

A further advantage of the data exchange via the data line 22 resides in the improved possibility of evaluating the measured values stored during an examination at the injector 4 or at the computed tomograph 2. These can be transmitted specifically from one device 2, 4 to the other, or be read out, and are combined to form a common, patient-specific and examination-specific protocol. This leads in the evaluation of the examination results to substantial time savings, and transmission errors are avoided, in particular. The examination result is preferably transmitted here directly into an electronic patient file, and serves as a basis for an electronic accounting program.

For the purpose of simplified operation, the data interface 20A, B is standardized to the effect that even devices 2, 4 of different types can communicate with one another via the common data line 22. This provides the possibility of also being able to connect different injectors 4 to a computed tomograph 2 without any problem. Particularly in combination with a common operating console 12A provided at the computed tomograph 2 and via which at least the central functions of the injector 4 are driven and important operating states of the injector 4 are also displayed, a standardized operator interface is provided for operating different injector types.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for data exchange between a computed tomograph and an injector, the method comprising:
   mutually exchanging data between the computed tomograph and the injector via a data interface, the data relating to respective operating states of the computed tomograph and the injector;
   transmitting a malfunction occurring during operation of one of the computed tomograph and the injector to an other of the computed tomograph and the injector, the malfunction being caused by failure of the injector; and
   automatically determining, using a termination rule, whether to terminate operation of the other of the computed tomograph and the injector based on an injected quantity of contrast agent at the time of the malfunction, and without regard to level of image enhancement.

2. The method as claimed in claim 1, wherein the data from one of the computed tomograph and the injector is used as a basis to control the operation of the other of the computed tomograph and the injector.

3. The method as claimed in claim 2, wherein decision parameters are provided for the termination rule, and values for the decision parameters being at least one of:
   adopted automatically from operational data of at least one of the computed tomograph and an injector,
   input manually before the start of the operation,
   determined in an organ-specific fashion taking account of an organ to be examined,
   determined in a patient-specific fashion and input, and
   determined with the aid of the protocol characterizing the carrying out of at least one of a scanning operation and an injection.

4. The method as claimed in claim 2, wherein current operational data of one of the computed tomograph and the injector are displayed on a display element at the other of the computed tomograph and the injector.

5. The method as claimed in claim 2, wherein one of the computed tomograph and the injector is provided with a common operating console with the aid of which it is also possible to drive the other of the computed tomograph and the injector.

6. The method as claimed in claim 2, wherein the data interface is standardized for the data exchange between the computed tomograph and the injector.

7. The method as claimed in claim 2, wherein after the carrying out of at least one of a scanning operation and an injection, a specific data protocol of one of the computed tomograph and the injector is transmitted to the other of the computed tomograph and the injector.

8. The method as claimed in claim 1, wherein before starting to operate one of the computed tomograph and the injector, an operational readiness of the other of the computed tomograph and the injector is checked.

9. The method as claimed in claim 8, wherein the start of the operation of one of the computed tomograph and the injector is automatically suppressed if the other of the computed tomograph and the injector is not operationally ready.

10. The method as claimed in claim 9, wherein decision parameters are provided for the termination rule, and values for the decision parameters being at least one of:
    adopted automatically from operational data of at least one of the computed tomograph and an injector,
    input manually before the start of the operation,
    determined in an organ-specific fashion taking account of an organ to be examined,
    determined in a patient-specific fashion and input, and
    determined with the aid of the protocol characterizing the carrying out of at least one of a scanning operation and an injection.

11. The method as claimed in claim 8, wherein decision parameters are provided for the termination rule, and values for the decision parameters being at least one of:
    adopted automatically from operational data of at least one of the computed tomograph and an injector,
    input manually before the start of the operation,
    determined in an organ-specific fashion taking account of an organ to be examined,
    determined in a patient-specific fashion and input, and
    determined with the aid of the protocol characterizing the carrying out of at least one of a scanning operation and an injection.

12. The method as claimed in claim 1, wherein decision parameters are provided for the termination rule, and values for the decision parameters being at least one of:
    adopted automatically from operational data of at least one of the computed tomograph and the injector,
    input manually before the start of the operation,
    determined in an organ-specific fashion taking account of an organ to be examined,
    determined in a patient-specific fashion and input, and
    determined with the aid of the protocol characterizing the carrying out of at least one of a scanning operation and an injection.

13. The method as claimed in claim 1, wherein current operational data of one of the computed tomograph and the injector are displayed on a display element at the other of the computed tomograph and the injector.

14. The method as claimed in claim 1, wherein one of the computed tomograph and the injector is provided with a common operating console with the aid of which it is also possible to drive the other of the computed tomograph and the injector.

15. The method as claimed in claim 1, wherein the data interface is standardized for the data exchange between the computed tomograph and the injector.

16. The method as claimed in claim 1, wherein after the carrying out of at least one of a scanning operation and an injection, a specific data protocol of one of the computed tomograph and the injector is transmitted to the other of the computed tomograph and the injector.

17. An apparatus comprising:
a computed tomograph; and
an injector, the computed tomograph and the injector being configured to,
    mutually exchange data relating to an operating state of the computed tomograph and the injector,
    transmit a malfunction occurring during the operation of one of the computed tomograph and the injector to an other of the computed tomograph and the injector, the malfunction being caused by failure of the injector, and
    automatically determine, using a termination rule, whether to terminate operation of the other of the computed tomograph and the injector based on an injected quantity of contrast agent at the time of the malfunction, and without regard to level of image enhancement.

18. An apparatus for data exchange between a computed tomograph and an injector, comprising:
means for mutually exchanging data between the computed tomograph and the injector via a data interface, the data relating to respective operating states of the computed tomograph and the injector;
means for transmitting a malfunction occurring during operation of one of the computed tomograph and the injector to an other of the computed tomograph and the injector, the malfunction being caused by failure of the injector; and
means for automatically determining, using a termination rule, whether to terminate operation of the other of the computed tomograph and the injector based on an injected quantity of contrast agent at the time of the malfunction, and without regard to level of image enhancement.

19. The apparatus as claimed in claim 18, wherein the data from one of the computed tomograph and the injector is used as a basis to control the operation of the other of the computed tomograph and the injector.

20. The apparatus as claimed in claim 18, wherein before starting to operate one of the computed tomograph and the injector, an operational readiness of the other of the computed tomograph and the injector is checked.

21. The apparatus as claimed in claim 20, wherein the start of the operation of one of the computed tomograph and the injector is automatically suppressed if the other of the computed tomograph and the injector is not operationally ready.

* * * * *